United States Patent [19]

Dallons et al.

[11] Patent Number: 5,118,821
[45] Date of Patent: Jun. 2, 1992

[54] PROCESS FOR THE PRODUCTION OF GAMMA-BUTYROLACTONE

[75] Inventors: Jean-Luc Dallons, Sint-Pieters-Leeuw; Pierre Jacobs, Gooik; Johan Martens, Brussels; Paul Tastenhoye, Tervuren; Ivan Vander Eynde, Keerbergen; August Van Gysel, Dilbeek, all of Belgium

[73] Assignee: U C B, S.A., Brussels, Belgium

[21] Appl. No.: 657,609

[22] Filed: Feb. 19, 1991

Related U.S. Application Data

[63] Continuation of Ser. No. 334,856, Apr. 6, 1989, abandoned.

[30] Foreign Application Priority Data

Apr. 22, 1988 [GB] United Kingdom ............... 8809587

[51] Int. Cl.$^5$ ........................................ C07D 307/33
[52] U.S. Cl. .................................................. 549/325
[58] Field of Search ........................................ 549/325

[56] References Cited

U.S. PATENT DOCUMENTS 3,994,928 11/1976 Michalczyk et al. ............... 549/325
4,087,476 5/1978 Hayes ................................... 260/668

FOREIGN PATENT DOCUMENTS 0159578 10/1985 European Pat. Off. .
0246031 11/1987 European Pat. Off. .
46-33030 9/1971 Japan .

Primary Examiner—C. Warren Ivy
Assistant Examiner—Ba K. Trinh
Attorney, Agent, or Firm—Wenderoth, Lind & Ponack

[57] ABSTRACT

A process for producing gamma-butyrolactone by catalytic hydrogenation of maleic anyhydride in the liquid phase with hydrogen, at a high temperature and under pressure, in the presence of a catalyst comprising nickel and palladium deposited on a support, wherein said support is a silica based support having a very high specific surface area, the value of which may range from 50 m$^2$/g, preferably from about 100 m$^2$/g to about 800 m$^2$/g and more.

Very high conversion rates of 90-98 mole % and excellent selectivities to gamma-butyrolactone of 95 to 97 mole % are achieved by the process.

13 Claims, No Drawings

PROCESS FOR THE PRODUCTION OF GAMMA-BUTYROLACTONE

This application is a continuation of now abandoned application Ser. No. 334,856 filed Apr. 6, 1986.

The present invention relates to a new process for producing gamma-butyrolactone by catalytic hydrogenation of maleic anhydride in the liquid phase.

It is well known that catalytic hydrogenation of maleic anhydride leads to various products such as succinic anhydride, gamma-butyrolactone, 1,4-butanediol and/or tetrahydrofuran, as well as other hydrogenation products of lesser value such as propanol, butanol, butyric acid, etc. and that numerous attempts have been made to obtain preferentially only one of these products of hydrogenation by using specific catalysts.

In order to obtain optimum yields of gamma-butyrolactone, it has been proposed to synthetize this product in two steps, proceeding first with the conversion of maleic anhydride into succinic anhydride at temperatures and pressures which are relatively low, and then effecting the conversion of succinic anhydride into gamma-butyrolactone at higher pressures and temperatures (see for example U.S. Pat. No. 4,025,534).

However, the two step process is of little technical and economical importance for several reasons.

Indeed, it is necessary to operate either in a single reactor, but providing different temperature zones according to the stage of progress of the reaction, or in two reactors operating under different operating conditions. In this latter case, it will also be necessary to provide some means for transporting the reaction mixture at high temperature and under pressure, from the reactor in which the succinic acid is synthetized to the reactor in which the gamma-butyrolactone is synthetized.

Therefore, it will be understood that it would be far more profitable to be able to convert maleic anhydride into gamma-butyrolactone directly, in a single step. However, to proceed in this way involves a considerable number of difficulties.

First, each successive hydrogenation reaction has its own kinetics and its own reaction conditions. Thus, the hydrogenation of succinic anhydride to gamma-butyrolactone requires much more severe operating conditions (temperatures and pressures considerably higher, and an increased amount of catalyst) than does the hydrogenation of maleic anhydride into succinic anhydride. For the direct conversion of maleic anhydride into gamma-butyrolactone, the quantity of catalyst required must therefore be adapted to the hydrogenation reaction of succinic anhydride into gamma-butyrolactone. If, however, such a quantity of catalyst is present, a significant amount of heat will be released in a very short period of time, because the hydrogenation reaction of maleic anhydride to succinic anhydride has a marked exothermic character. In fact, this reaction releases about 32.3 kcal per mole of succinic anhydride formed. First of all, therefore, the catalyst which it is proposed to use for the direct conversion of maleic anhydride into gamma-butyrolactone must be able to resist this exothermic effect, so that it shall have a reasonable useful life, otherwise the profitability of the process will be seriously affected.

Secondly, it is well known that gamma-butyrolactone is only an intermediate product of the hydrogenation reaction, and that it can in its turn become hydrogenated into 1,4-butanediol and/or to tetrahydrofuran.

Now, the subsequent reaction leading to 1,4-butanediol must be avoided, given that this diol reacts with the unconverted succinic anhydride to form esters having no value, which require an elaborate method of separation and furthermore constitute a potential catalyst poison. It is also known that the hydrogenation reaction may lead to a certain number of less valuable byproducts, such as propanol, butanol, propionic acid, butyric acid and the like.

It is thus essential that the catalyst used shall be highly selective for the production of gamma-butyrolactone, thus minimizing the formation of these undesirable by-products.

It will be noted that in order to stop the conversion process at the desired product, i.e. gamma-butyrolactone, it would be possible to carry out the hydrogenation at a low conversion rate. However, this way of operating would cause severe technological problems, given the low solubility of succinic anhydride and its high melting point (119.6° C.). In addition, at a low conversion rate, it would be mandatory to operate with numerous recycling steps, which would be detrimental to the productivity of the process and would also necessitate the use of heated tubes, significantly increasing the manufacturing costs. Therefore, the catalyst used must not only be very selective, but it must at the same time be highly active in order to achieve very high conversion rates, if possible exceeding 90%.

Finally, it is known that the formation of by-products such as propionic acid and butyric acid increases when hydrogenation is carried out at relatively high temperatures. Therefore, it is desirable that the catalyst be active at quite low temperatures so as to minimize the formation of these by-products.

Likewise, it is desirable that hydrogenation can be carried out at relatively low pressures in order to minimize the costs of the plant and of operation (apparatus, compressors, etc.).

In conclusion, the difficulty is to find a catalyst which enables gamma-butyrolactone to be produced profitably from maleic anhydride.

An ideal catalyst for this purpose would have to meet the following requirements:

(1) it should be able to convert maleic anhydride directly to gamma-butyrolactone in a single step;
(2) it should be highly selective for the production of gamma-butyrolactone (93 mole % and more), thus minimizing the formation of by-products:
(3) it should be sufficiently active to be able to effect the reaction at very high conversion rates, preferably greater than 90 mole %;
(4) it should be active at relatively low temperatures (for example, within the range of from 200° to 240° C.) and at relatively low pressures (for example, at pressures below 100 bars)
(5) it should have a long active life (i.e. without appreciable deactivation)
(6) its cost price should be acceptable.

When the state of the art in this field is examined, it is found that most of the known catalysts do not give entire satisfaction in respect of all of the above-mentioned requirements. By way of example, in U.S. Pat. No. 3,948,805, it is proposed to convert maleic anhydride to gamma-butyrolactone in a single step, in the presence of a catalyst which has a high selectivity for the production of gamma-butyrolactone (93 to 96 mole %). However the catalyst composition used in order to obtain this result is highly complex. Indeed, it comprises two distinct catalysts having four catalytically active elements, the first catalyst being based on nickel and copper chromite deposited on aluminum oxide and on kieselguhr, while the second catalyst is based on palladium supported on activated carbon. In addition, according to the working examples, the hydrogenation of maleic anhydride is effected under relatively high pressures which may vary from 100 to 150 bars. In U.S. Pat. No. 4,096,156, there are also disclosed very high selectivities in the conversion of maleic anhydride to gamma-butyrolactone (90 mole % and more), but these selectivities are obtained as a result of the use of very expensive catalysts which include considerable amounts of several noble metals. According to the examples, these catalysts contain about 11.8% by weight of palladium (or 5.7% by weight of palladium together with about 9.8% by weight of platinum) and 2.5 to 5.2% by weight of silver and/or gold, in metallic form. Moreover, the hydrogenation of maleic anhydride is carried out under very high pressures (189 to 215 bars). In U.S. Pat. No. 3,994,928, a catalyst is proposed which is composed of cobalt oxide and palladium deposited on kieselguhr or on $SiO_2$ spherical pellets from 2 to 3 mm in diameter. The cost of this catalyst is more acceptable, but according to the working examples, the conversion of maleic anhydride to gamma-butyrolactone is carried out at a temperature of 250° C. and at 150 atmospheres pressure: therefore, if this process were to be applied on an industrial scale, it would require very elaborate and, consequently, very expensive engineering. In various other patents, catalysts have also been proposed for the catalytic hydrogenation of succinic anhydride to gamma-butyrolactone (published Japanese patent application No. 33030)71; U.S. Pat. No. 4,620,017). However, in these processes, maleic anhydride has first to be converted to succinic anhydride in a separate production unit in which a possibly different catalyst is used.

As has already been explained above, it is of far greater technical and economic importance to provide a process and a catalyst that allow direct conversion of maleic anhydride to gamma-butyrolactone in a single step.

In published Japanese patent application 33030/71, there is described the preparation of bi-metallic catalysts composed of nickel and a precious metal selected from palladium, ruthenium, platinum and osmium. These catalysts can be used in the absence of a support material, but preference is given to supported catalysts. As a support material, mention is made of silica gel, alumina and silica-alumina, but diatomaceous earth is preferably used. In the sole example given in this patent application, catalysts prepared are used in the catalytic hydrogenation of succinic anhydride at a temperature of 260° C. and under a pressure of 120 kg/cm². The best result is obtained with a catalyst composed of nickel and palladium. However, its selectivity for the production of gamma-butyrolactone remains quite low: it hardly reaches 70 mole I and a not insignificant amount of by-products is also formed (6.6 mole % of tetrahydrofuran, 2.8 mole % of n-propanol and 24.1 mole % of other unidentified products) and all of this in spite of the fact that the catalyst used contains more than 50% by weight of metal (nickel and precious metals) based on the total weight of the catalyst (i.e. metals plus support material).

According to the present invention, we have made the surprising discovery that, by using also nickel in combination with palladium as the catalytically active elements of the catalyst, but selecting however a silica having a very high specific surface area as support material, it is possible to make an excellent catalyst which meets all the technical and economic requirements set out above in points (1) to (6), and which can therefore be used with great advantage in the production of gamma-butyrolactone from maleic anhydride in a single step.

Therefore, according to the present invention, there is provided a new lo process for producing gamma-butyrolactone by catalytic hydrogenation which comprises reacting maleic anhydride in the liquid phase with hydrogen at a high temperature and under pressure, in the presence of a catalyst comprising nickel and palladium deposited on a silica based support material having a specific surface area of at least 50 m²/g, and preferably at least 100 m²/g.

In contrast with the catalysts used in published Japanese patent application No. 33030/71, the nickel-palladium catalyst used in the process according to the present invention is deposited on a silica based support having a very high specific surface area, the value of which may range from 50 m²/g, preferably from about 100 m²/g to about 800 m²/g and more.

We have found, indeed, that the nickel-palladium catalyst becomes highly active when it is deposited on a silica based support with a high specific surface area, which results in very high conversion rates being obtained these being of the order of 90 to 98 mole % with, in addition, excellent selectivities for the production of gamma-butyrolactone of 95 to 97 mole % (as compared with a maximum of 69.5 mole % of butyrolactone formed in published Japanese patent application No. 33030/71). It has also been found that the temperature and pressure at which the catalyst is active for hydrogenation of maleic anhydride are lower, and that very favorable results can be obtained when operating at a temperature of from 200° to 240° C. and at a pressure of from 50 to 100 bars.

Furthermore, it has been observed that remarkable results can be obtained with catalysts in which the nickel content (calculated as metal) is only in the range of from 8 to 25% by weight, and the palladium content (calculated as metal) is only in the range of from 0.5 to 4% by weight, based on the total weight of the supported catalyst. The amount of metal (nickel and precious metal) required for preparation of the nickel-palladium catalysts which are used according to the invention, is thus markedly lower as compared with that required for the catalysts described in published Japanese patent application No. 33030/71, and this represents an obvious economic advantage.

It is totally unexpected that it is possible to obtain a considerable increase in the activity of the nickel-palladium catalyst as a result of the use of a silica based support material having a high specific surface area, because in many patents relating to the hydrogenation of maleic anhydride, preference is given to diatomaceous earth (published Japanese patent application No. 33030/71) or to similar support materials such as kieselguhr, having a low specific surface area of 0.1 to 10 m²/g (see for example U.S. Pat. No. 4,096,156, column 3, lines 19-21).

More recently, in U.S. Pat. No. 4,620,017, there has also been proposed as support material a silica having a specific surface area of at least 50 m$^2$/g. In that patent, it is shown that the incorporation of zirconium or cerium into a nickel catalyst, deposited on a silica support having a specific surface area of 300 m$^2$/g, has a significant beneficial effect on the selectivity to gamma-butyrolactone.

However, that patent does not teach the beneficial function of the high specific surface area of the silica support on the activity of the catalyst, on the discovery of which the process according to the invention mainly rests. In that patent, the silica having a high specific surface area has obviously no other function than to serve as a support.

Finally, it will be noted that the beneficial effect of the support mainly composed of silica having a high specific surface area on the activity of the catalyst is closely related to the nature of the metals used in the composition of the catalyst. We have found, indeed, that the beneficial effect of the silica based support having a high specific surface area is in no way obtained if, in the catalyst, either the nickel is replaced with cobalt, or the palladium is replaced with other active catalytic elements such as platinum or molybdenum.

It is now proposed to describe in greater detail the catalyst and its preparation, as well as the process for catalytic hydrogenation of maleic anhydride according to the present invention.

1. Catalyst

The catalyst used in the process of the present invention contains, as catalytically active elements, nickel and palladium in metallic form. The raw materials used in the preparation of the catalyst are compounds which are soluble in water and which are capable of giving the elements Ni and Pd in metallic form by thermal reduction. Compounds of this kind include, for example, the following:

for nickel: nitrates, formates, oxalates, tartrates, citrates and the like:

for palladium: chlorides, amine complexes such as palladium (II) tetrammine chloride, [Pd(NH$_3$)$_4$]Cl$_2$, and the like. According to the present invention, the catalytically active elements (nickel and palladium) are used on a silica based support having a specific surface area of at least 50 m$^2$/g, preferably of at least 100 m$^2$/g (determined by the B.E.T./N$_2$ method: ASTM D 3663-84). The preferred silica based supports have specific surface areas which range from about 100 m$^2$/g to about 800 m$^2$/g and more. The silica based support materials having a high specific surface area which may be used according to the invention have a SiO$_2$ content of at least 70% by weight. The preferred supports contain from 75 to 100% by weight of SiO$_2$. When the support having a high specific surface area does not consist entirely of silica, the latter is associated with other refractory inorganic oxides, such as aluminum oxide, titanium dioxide, etc. These supports having a high specific surface area can be obtained by methods known per se, such as for example the method described by A. J.. LEONARD et al in Discussions Faraday Soc.52,(1971),98-108. By way of example, a silica having a high specific surface area can be obtained from tetraethyl ortho-silicate by hydrolysis with a solution of an acid, such as acetic acid, at a temperature of 80° to 90° C. and calcination of the gel thus obtained at temperatures between 400° and 1000° C. It is also possible to use supports having a high specific surface area which are commercially available these are sold for example by RHONE-POULENC, DEGUSSA. W.R. GRACE Inc. and REDCO N.V. The supports used according to the invention are in powder form, with a particle size of between 5 and 100 μm. When supports of different chemical composition are used, such as for example aluminum oxide, magnesium oxide, aluminum phosphate, aluminosilicates having a low SiO$_2$ content, or zeolites, a sharp drop in the activity of the catalyst has been observed. The nickel content (calculated as metal) of the catalyst generally ranges from about 5 to about 50% by weight preferably from 7 to 40% by weight, based on the total weight of the supported catalyst: its palladium content (calculated as metal) generally ranges from about 0.4 to about 7% by weight, preferably from 0.5 to 4% by weight, based on the total weight of the supported catalyst. As will be seen below in the working examples, excellent results can be obtained with catalysts having a nickel content (calculated as metal) which ranges only from 8 to 25% by weight, and of which the palladium content (calculated as metal) ranges only from 0.5 to 4% by weight, based on the total weight of the supported catalyst.

2. Preparation of the catalyst

The metallic components of the catalyst can be deposited on the silica based support according to methods well known to those skilled in the art. Thus, for example, there can be started by impregnating the support in powder form with an aqueous solution containing a compound of one of the two metals, then drying the paste thus obtained, impregnating the dry powder with an aqueous solution of a compound of the other metal, and finally once again drying the paste thus obtained. However, one might just as well impregnate the support with an aqueous solution containing both metal compounds at the same time, followed by a single drying step of the paste thus obtained. Also, it can be envisaged that the nickel compound be first precipitated on to the support, followed by the palladium compound, and vice versa. It is clear that the deposition of the metallic components on the support can be carried out in any order. The drying operations can be performed in the presence of air, at a temperature of 80° to 150° C. for a time of from 3 t20 hours. Next, the supported catalytic material is calcined in the presence of a gas containing oxygen, for example air, at a temperature of 300° to 750° C. for a time of 0.5 to 3 hours, and preferably at a temperature of 400 to 500° C. for a time of 1 to 2 hours. Under this oxidizing treatment, the Ni and Pd compounds contained in the silica based support are converted into oxides. At the end of this oxidizing treatment, the catalyst is reduced with pure hydrogen or with a gaseous mixture containing hydrogen and nitrogen, the hydrogen content of which may vary between 5 and 100% by volume. This reduction is carried out at a temperature of between 300° and 750° C. for 0.5 to 5 hours, preferably at a temperature of 400° to 550° C. for 1 to 3 hours. The catalyst is then cooled in a stream of the reducing gas down to a temperature in the range between 80° and 150° C. At this temperature, the reducing gas is replaced by a stream of CO$_2$ for 5 to 20 hours. After this, the catalyst is allowed to cool in the CO$_2$ stream down to ambient temperature, and the CO$_2$ is progressively replaced by air. The catalyst, when ready for use, is in the form of a powder having a particle size of 5 to 30 μm.

3. Catalytic hydrogenation of maleic anhydride

According to the present invention, the catalytic hydrogenation of maleic anhydride is carried out in the liquid phase with hydrogen under heat and pressure and in the presence of the supported catalyst described above. The latter is introduced into the liquid phase in powder form to produce a suspension. It is known that maleic anhydride is a solid substance at ordinary temperatures (its melting point is about 52.5° C.). In order to achieve hydrogenation in the presence of a catalyst in suspension, it is possible to use only maleic anhydride in a molten state. However, this procedure gives rise to difficulties in controlling the exothermic effect of the first hydrogenation (from maleic anhydride to succinic anhydride), with a risk of a considerable elevation of the temperature. For this reason, according to a preferred form of the process according to the invention, the catalytic hydrogenation of the maleic anhydride is carried out in solution, either in a solvent which is inert to the reaction, or in the product of the reaction. The process can be performed in a large number of solvents. Preferably, the solvent is selected from the following compounds, used alone or as a mixture: dioxane tetrahydrofuran, gamma-butyrolactone, aliphatic hydrocarbons, etc. In general the concentration of maleic anhydride in the solvent may vary between 10 and 90% by weight and preferably between 40 and 60% by weight. In addition, the amount of catalyst used in putting the process according to the invention into practice may vary between 1 and 30% by weight of the maleic anhydride subjected to the hydrogenation. This amount will lie advantageously between 5 and 15% by weight of the maleic anhydride. An essential advantage from the technical point of view of the process according to the invention, is that it is carried out at pressures lower than 100 bars, that is to say under pressures markedly lower than those applied in the state of the art, and this enables the use of conventional reactors and instruments which are convenient and economical in operation and maintenance. In the method chosen for industrial exploitation, the operating pressure will advantageously vary in the range of from about 50 to 100 bars. One essential operational feature of the process according to the invention is also the maintenance of a hydrogenation temperature between 180° and 270° C., preferably between 200° and 240° C. It is possible to operate at a higher temperature, but it has been found that the selectivity for the production of gamma-butyrolactone decreases for the benefit of the formation of by-products such a butyric acid. On the other hand, if the process is carried out below 180° C., the speed of the reaction decreases, which requires a longer reaction time and leads to a reduction of the productivity of the reaction apparatus. According to the invention, the process for the catalytic hydrogenation of maleic anhydride to gamma-butyrolactone is carried out for example in the following manner: The desired amount of maleic anhydride, solvent and catalyst are added into a reactor, for example an autoclave provided with an agitation system, and then the reactor is flushed out with nitrogen. The nitrogen is then replaced by hydrogen at a pressure of 50 bars, and the agitating means and heating means are put into operation. When the temperature has reached 200° to 240° C. an additional amount of hydrogen is introduced in order to keep the reaction pressure constant at about 95 bars throughout the whole duration of the reaction. The reaction time is regulated so as to obtain a conversion rate of more than 90 mole %. Depending upon the operating parameters selected, the reaction time is between 1 and 10 hours, preferably between 1.5 and 3.5 hours. At the end of the reaction, the contents of the autoclave are cooled and relieved of pressure, the catalyst is separated by filtration and the filtrate is recovered. Subsequently, the catalyst is recycled for use in a further hydrogenation under the same conditions. If after several runs it is found that the catalyst has undergone a loss of activity, part of it is replaced by fresh catalyst to restore its activity. On the other hand, the filtrate is subjected to separation, for example by fractional distillation, in order to recover the gamma-butyrolactone. In the process according to the invention, conversion rates of 90 to 98 mole % can very easily be obtained at the same time, very high selectivities can be obtained for the production of gamma-butyrolactone, which are always higher than 93 mole % and most often reach 95 to 97 mole Only a very small amount of by-products (propionic acid, butyric acid) is formed, and this greatly facilitates the operation of purifying the gamma-butyrolactone.

The process of the invention also has considerable economic importance, because the catalyst has excellent stability and may be recycled numerous times without any substantial decrease of its catalytic performance (see example 6 below).

The following working examples are given for the purpose of illustrating the present invention without limiting it. In these examples, the following definitions are used:

$$\text{Conversion (in mole \%)} = 100 - \frac{\text{moles of uncovered SA} \times 100}{\text{moles of MA fed}}$$

Selectivity to gamma-butyrolactone (in mole %) =

$$100 \times \frac{\text{moles of GBL produced}}{\text{moles of MA fed} - \text{moles of unconverted SA}}$$

SA = succinic anhydride
MA = maleic anhydride
GBL = gamma-butyrolactone.

(In practice, it is the conversion of succinic anhydride that is determined, because under the reaction conditions, conversion of maleic anhydride is always 100%).

EXAMPLE 1 PREPARATION OF THE CATALYST

This example illustrates two methods of preparation of the supported nickel palladium catalyst used according to the invention.

(a) 148.6 g of nickel nitrate [$(NiNO_3)_2.6H_2O$] are dissolved in 185.8 ml of distilled water. 100 g of silica support are impregnated with this solution, the support having a specific surface area (BET/$N_2$) of 570 m$^2$/g (the support being prepared according to the method described by A. J. LEONARD et al in Discussions Faraday Soc.52,(1971). pages 98–108. from tetraethyl orthosilicate by hydrolysis with acetic acid solution at a temperature of about 82° C., followed by calcination of the gel thus obtained at a temperature of 500° C.). The whole is carefully mixed, and the paste thus obtained is dried in an oven at 100° C. for 15 hours, 7.15 of [$Pd(NH_3)_4$]$Cl_2$ are dissolved in 185.8 ml of distilled water, and the powder containing the nickel salt and the support is impregnated with this solution. The paste obtained in this way is dried in an oven at 100° C. for 15 hours. A powder is thus obtained which is calcined in the presence of air for 3 hours at 450° C. The resulting calcined powder is allowed to cool, and then reduction of the catalyst is carried out. To this end, the air is replaced by a hydrogen stream at a flow rate of 75 ml per minute, and the temperature of the oven is set at 450° C. The hydrogen stream is maintained at this temperature for 1 hour. The catalyst is cooled in a hydrogen stream until temperature has been reduced to 100° C. At this temperature, the hydrogen is replaced by a $CO_2$ stream at a flow rate of 10 ml per minute. The $CO_2$ stream is maintained for 15 hours. Subsequently, the catalyst thus obtained is cooled down to ambient temperature. $CO_2$ is then progressively replaced by air. The catalyst thus prepared contains 22.54% by weight of Ni and 2.33% by weight of Pd, calculated with respect to the total weight of the supported catalyst. This catalyst is in the form of a powder. Hereinbelow, this catalyst is designated "catalyst A".

(b) 148.6 g of nickel nitrate $(Ni(NO_3)_2.6H_2O)$ are dissolved in 145.3 ml of distilled water. In addition, 7.15 g of $[Pd(NH_3)_4]Cl_2$ are dissolved in 40.5 ml of distilled water. These two solutions are mixed together. 100 g of the silica support described in (a) above and having a specific surface area of 570 m$^2$/g are impregnated with this solution. The whole is carefully mixed, and the paste thus obtained is dried in an oven at 100° C. for 15 hours. Subsequent treatment (calcination, reduction and passivation) is exactly identical with that described for catalyst A. The catalyst thus prepared contains the same quantities by weight of nickel and palladium as catalyst A. This catalyst is hereinafter referred to as "catalyst B".

EXAMPLE 2 PREPARATION OF GAMMA-BUTYROLACTONE (a) In the presence of catalyst A from example 1

56 g of maleic anhydride, 56 g of tetrahydrofuran and 5.6 g of catalyst A, prepared according to example 1 (a), are introduced into a stainless steel autoclave of 300 ml capacity, provided with a magnetic agitation system and an electric heating mantle. The contents of the reactor are flushed out with nitrogen and then with hydrogen, after which the pressure in the reactor is raised to 50 bars with hydrogen. The temperature of the mixture is then progressively raised to 235° C. the mixture being agitated, with the pressure being maintained at 50 bars by a hydrogen supply. When a temperature of 235° C. is reached, the pressure in the reactor is raised to 95 bars, and this temperature is kept constant by the regulating system of the electric heating mantle of the reactor. After 3 hours of reaction (including the heating time), the reaction mixture is cooled down to ambient temperature, and the catalyst is filtered. Analysis of the reaction mixture is carried out by gas chomatography and by high pressure liquid phase chromatography. The conversion is 95 mole %, and the selectivity to gamma-butyrolactone is 96 mole %.

(b) In the presence of catalyst B from example 1

The process is exactly the same as in (a) above, but catalyst B, prepared according to example 1 (b), is used. According to the analysis of the reaction mixture, the conversion is 96 mole %, and the selectivity to gamma-butyrolactone is 97 mole %.

EXAMPLE 3 EFFECT OF THE SPECIFIC SURFACE AREA OF THE SUPPORT ON THE ACTIVITY OF THE CATALYST

In this example, the effect of the specific surface area of the support on the activity of the catalyst is demonstrated.

To this end, a comparison will be made between the catalytic performances of a series of nickel-palladium catalysts deposited on silica supports having specific surface areas (BET/$N_2$) in the range from 120 to 770 m$^2$/g (according to the invention), and those of nickel-palladium catalysts deposited on kieselguhr (supplied by RIEDEL-de HAEN A.G.), having a specific surface area (BET/$N_2$) of only 10 m$^2$/g (not according to the invention).

All the catalysts according to the invention were prepared according to the process described in example 1 (a). However, in order to obtain different specific surface areas, calcination of the support was carried out respectively at 900° C. (catalyst C), 700° C. (catalyst D), 500° C. (catalyst E) and 400° C. (catalyst F).

The catalytic hydrogenation of maleic anhydride was carried out under the same conditions as in example 2 (reaction time: 3 hours). Table I below shows, for each catalyst used, the quantity in % by weight of nickel and of palladium calculated with respect to the total weight of the supported catalyst, the nature of the support, its specific surface area BET/$N_2$ (in m$^2$/g), and also the conversions and the selectivities (in mole %) obtained in preparation of gamma-butyrolactone.

TABLE I

| Catalyst | Quantity of metal (% by weight) | | Support | | Conversion (mole %) | Selectivity (mole %) |
| --- | --- | --- | --- | --- | --- | --- |
| | Ni | Pd | Nature | Specific surface area (m$^2$/g) | | |
| C | 16.26 | 2.06 | $SiO_2$ | 120 | 92 | 94.7 |
| D | 16.26 | 2.06 | $SiO_2$ | 320 | 87 | 93.8 |
| E | 16.26 | 2.06 | $SiO_2$ | 570 | 92 | 95.2 |
| F | 22.5 | 2.33 | $SiO_2$ | 770 | 95 | 93,6 |
| 1 | 16.26 | 2.06 | Kieselguhr | 10 | 62 | — |
| 2 | 22.5 | 0.96 | Kieselguhr | 10 | 60 | — |
| 3 | 22.5 | 1.3 | Kieselguhr | 10 | 62 | — |
| 4 | 22.5 | 2.33 | Kieselguhr | 10 | 61 | — |

This table clearly shows that the activity of the nickel-palladium catalyst is considerably increased by using as a support a silica having a high specific surface area.

It can be seen, indeed, that the conversions obtained (87 to 95 mole %) with catalysts C to F deposited on a silica support having a high specific surface area (according to the invention) are markedly superior to those obtained with catalysts 1 to 4 deposited on a kieselguhr support having a low specific surface area (60 to 62 mole %) which are used for purposes of comparison.

For comparison purposes, there were also prepared catalysts deposited on a silica support with a high specific surface area (570 m$^2$/g) in accordance with the process described in example 1 (a), but in which (1) the palladium was replaced by platinum (comparative catalyst 5) or by molybdenum (comparative catalysts 7 and 8), (2) the nickel was replaced by cobalt (comparative catalyst 6).

The catalytic hydrogenation of maleic anhydride was carried out under the same conditions as in example 2 (reaction time: 3 hours).

Table II shows the results obtained.

TABLE II

| Cat-alyst | Quantity of metal (% by weight) | | | | | Conversion (mole %) | Selectivity (mole %) |
|---|---|---|---|---|---|---|---|
| | Ni | Co | Mo | Pd | Pt | | |
| E | 16.26 | — | — | 2.06 | — | 92 | 94.7 |
| 5 | 16.26 | — | — | — | 2.06 | 52.7 | 93.8 |
| 6 | — | 16.26 | — | 2.06 | — | 45 | 95.0 |
| 7 | 16.39 | — | 1.69 | — | — | 61.3 | 94.6 |
| 8 | 50.77 | — | 5.20 | — | — | 62 | 95.2 |

It is clearly apparent that catalysts 5 to 8 based on metals other than nickel or palladium exhibit only a low activity when the support is silica having a high specific surface area. The conversion (of 45 to 62 mole %) do not exceed those obtained with the nickel-palladium catalysts deposited on a kieselguhr support having a low specific surface area. The beneficial effect of the silica having a high surface area on the catalytic activity thus appears to be closely related to the nature of the metals used in the composition of the catalyst.

EXAMPLE 4 INFLUENCE OF THE AMOUNT OF NICKEL AND PALLADIUM

For this test, a series of catalysts is used which are prepared exactly as described in example 1 (a), using the same starting materials, but different proportions, in such a way to cause the amount of metal (nickel and palladium) deposited on the silica support having a high specific surface area (BET/$N_2$) of 570 $m^2/g$, to be varied: the hydrogenation of the maleic anhydride is carried out under the same conditions of apparatus, temperature and pressure as in example 2.

Table III shows, for each of the catalysts used, the quantity of nickel and palladium in % by weight, calculated with respect to the total weight of the supported catalysts, the reaction time required, and also the results obtained in the preparation of gamma-butyrolactone.

TABLE III

| Catalyst | Quantity of metal (% by weight) | | Reaction time (min) | Conversion (mole %) | Selectivity (mole %) |
|---|---|---|---|---|---|
| | Ni | Pd | | | |
| G | 22.5 | 0.96 | 300 | 87.4 | 96.4 |
| H | 22.5 | 1.9 | 180 | 92.4 | 95.9 |
| I | 22.5 | 2.33 | 180 | 95.4 | 96.0 |
| J | 8.89 | 2.30 | 330 | 89.6 | 96.0 |

Table III shows that it is possible to obtain excellent conversions (87 to 96 mole %) and very high selectivities of 96 mole % to gamma-butyrolactone with catalysts in which the nickel content (calculated as metal) varies from 8 to 25% by weight, and in which the palladium content (calculated as metal) varies from 0.8 to 2.5% by weight, based on the total weight of the supported catalyst.

EXAMPLE 5 INFLUENCE OF THE HYDROGENATION TEMPERATURE

The operation is carried out under the same conditions as in example 2, but varying the temperature and the reaction time. Catalyst K used in this test is prepared by the process described in example 1 (a), but it contains 16.42I by weight of nickel and 1.04% by weight of palladium, calculated with respect to the weight of the supported catalyst.

The results obtained are set out in Table IV:

TABLE IV

| Catalyst | Temperature (°C.) | Reaction time (min) | Conversion (mole %) | Selectivity (mole %) |
|---|---|---|---|---|
| K | 235 | 360 | 92.6 | 96 |
| K | 270 | 120 | 93 | 93 |

It can be seen that at more elevated temperature (270° C.), the selectivity to gamma-butyrolactone decreases. This loss of selectivity is due to the production of by-products, and particularly of butyric acid. This product is very difficult to separate from the gamma-butyrolactone by distillation, because its boiling point is very close to that of gamma-butyrolactone.

EXAMPLE 6 RECYCLING OF THE CATALYST

The catalytic hydrogenation of maleic anhydride is carried out under the same conditions as in example 2 (reaction time: 3 hours), using catalyst A prepared according to the process described in example 1 (a). However, after separation of the catalyst by filtration, it is recycled in order to carry out a new hydrogenation under the same conditions. This operation is repeated 30 times.

Table V shows the performance of the catalyst in the course of these various operations:

TABLE V

| Number of recycling steps | Conversion (in mole %) | Selectivity (mole %) |
|---|---|---|
| — | 94.7 | 96 |
| 1 | 95 | 97 |
| 5 | 93.3 | 97.1 |
| 10 | 96.2 | 94.9 |
| 15 | 94.1 | 95.2 |
| 20 | 94.0 | 96.1 |
| 25 | 93.9 | 95.6 |
| 30 | 93.2 | 95.7 | it can be seen that the catalyst can be recycled numerous times without any sign of appreciable deactivation. After being recycled 30 times, the catalyst retains its activity and its selectivity in an excellent way. Example 7. Influence of the chemical composition of the support, on the activity of the catalyst is demonstrated. For this test, a series of catalysts prepared exactly as described in example 1 (a) are used, with the same quantities of metals, but deposited on supports having a different chemical composition or origin.

The catalytic hydrogenation of the maleic anhydride is carried out under the same conditions as in example 2 (reaction time: 3 hours).

Table VI indicates, for each catalyst used, the chemical composition of the support, its origin, its specific surface area BET/$N_2$ (in $m^2/g$), and also the conversions and the selectivities (in mole %) obtained during the preparation of gamma-butyrolactone.

TABLE VI

| Catalyst | Support Chemical composition | Support Origin | Specific surface area ($m^2/g$) | Conversion (mole %) | Selectivity (mole %) |
|---|---|---|---|---|---|
| L | $SiO_2$ | * | 610 | 95.4 | 95.1 |
| M | $SiO_2$ | W. R. GRACE, Inc. (Silica Gel 239) | 390 | 90 | 97.1 |
| N | $SiO_2/Al_2O_3$ (87/13) | * | 345 | 95 | 95.4 |
| O | $SiO_2/Al_2O_3$ (86.5/13.5) | REDCO N.V. (XONOSIAL) | 440 | 98 | 94.7 |
| 9 | $SiO_2/Al_2O_3$ (50/50) | * | 320 | 85 | 94 |
| 10 | $Al_2O_3$ | * | 230 | 35 | 93 |
| 11 | MgO | * | 310 | 40 | 94.2 |
| 12 | Zeolite (NaY) | UNION CARBIDE | 800 | 51.5 | 92.7 |

*these supports were prepared according to the process described in example 1 (a).

It can be seen that the conversions obtained (90 to 98 mole %) with catalysts L to O deposited on a silica based support (according to the invention), are markedly superior to those obtained with catalysts 9 to 12 deposited on a support of a different composition (not according to the invention), in spite of the fact that these latter have a specific surface area higher than 200 $m^2/g$.

Moreover, it can be seen that an improved conversion is only obtained on the condition that a silica based support containing a high proportion of $SiO_2$ is used. In addition, it is clear that the origin of the silica based supports has little influence on the results.

We claim:

1. A process for producing gamma-butyrolactone by catalytic hydrogenation, which comprises reacting maleic anhydride in the liquid phase with hydrogen, at high temperature and under pressure, in the presence of a catalyst comprising nickel and palladium deposited on a silica based support having a specific surface area of at least 50 $m^2/g$.

2. A process according to claim 1, wherein said support is a silica based support having a specific surface area of at least 100 $m^2/g$.

3. A process according to claim 1, wherein the specific surface area of the silica based support ranges from about 100 $m^2/g$ to about 800 $m^2/g$.

4. A process according to claim 1, wherein the $SiO_2$ content of the support ranges from 70 to 100% by weight, the balance being another refractory inorganic oxide.

5. A process according to claim 1, wherein said support is a substantially pure silica.

6. A process according to claim 1, wherein the nickel content of the catalyst ranges from about 5 to about 50% by weight, based on the total weight of the supported catalyst, and the palladium content of the catalyst ranges from about 0.4 to about 7% by weight, based on the total weight of the supported catalyst.

7. A process according to claim 6, wherein the nickel content of the catalyst ranges from 7 to 40% by weight, based on the total weight of the supported catalyst and the palladium content of the catalyst ranges from 0.5 to 4% by weight, based on the total weight of the supported catalyst.

8. A process according to claim 6, wherein the nickel content of the catalyst ranges from 8 to 25% by weight, based on the total weight of the supported catalyst and the palladium content of the catalyst ranges from 0.5 to 4% by weight, based on the total weight of the supported catalyst.

9. A process according to claim 1, wherein the hydrogenation is carried out at a temperature of from 180° to 270° C. and at a pressure of from about 50 to 100 bars.

10. A process according to claim 1, wherein the hydrogenation is carried out at a temperature of from 200° to 240° C. and at a pressure of from about 50 to 100 bars.

11. A process according to claim 1, wherein the hydrogenation is carried out in a solvent which is inert to the reaction or in the product of the reaction.

12. A process according to claim 1, wherein the amount of catalyst used is from 1 to 30% by weight of the maleic anhydride subjected to the hydrogenation.

13. A process according to claim 12, wherein the amount of catalyst used is from 5 to 15% by weight of the maleic anhydride subjected to the hydrogenation.

* * * * *